United States Patent
Xie Staehelin et al.

(10) Patent No.: US 11,254,909 B2
(45) Date of Patent: Feb. 22, 2022

(54) RHIZOBIUM AND USE AND BACTERIAL PREPARATION THEREOF, AND METHOD FOR RESTORING RARE-EARTH TAILING SOIL OR SILICA ORE TAILING WASTE

(71) Applicant: Bontech Welfare Academy of Environmental Science (Beijing) Co., Ltd., Beijing (CN)

(72) Inventors: Zhiping Xie Staehelin, Beijing (CN); Shaozhan Zhou, Beijing (CN); Suihua Wang, Beijing (CN)

(73) Assignee: Bontech Welfare Academy of Environmental Science (Beijing) Co., Ltd., Beijing (CN)

( * ) Notice: Subject to any disclaimer, the term of this patent is extended or adjusted under 35 U.S.C. 154(b) by 0 days.

(21) Appl. No.: 16/768,590

(22) PCT Filed: Nov. 23, 2018

(86) PCT No.: PCT/CN2018/117249
§ 371 (c)(1),
(2) Date: May 29, 2020

(87) PCT Pub. No.: WO2019/109822
PCT Pub. Date: Jun. 13, 2019

(65) Prior Publication Data
US 2021/0000122 A1    Jan. 7, 2021

(30) Foreign Application Priority Data
Dec. 4, 2017 (CN) .......................... 201711261668.1

(51) Int. Cl.
| | | |
|---|---|---|
| C12N 1/20 | (2006.01) | |
| A01N 63/00 | (2020.01) | |
| C09K 17/14 | (2006.01) | |
| A01N 63/20 | (2020.01) | |
| C09K 101/00 | (2006.01) | |
| C12R 1/41 | (2006.01) | |
| C12R 1/01 | (2006.01) | |

(52) U.S. Cl.
CPC ............ *C12N 1/205* (2021.05); *A01N 63/20* (2020.01); *C09K 17/14* (2013.01); *C12N 1/20* (2013.01); *C09K 2101/00* (2013.01); *C12R 2001/01* (2021.05); *C12R 2001/41* (2021.05)

(58) Field of Classification Search
None
See application file for complete search history.

(56) References Cited

U.S. PATENT DOCUMENTS

| | | | | |
|---|---|---|---|---|
| 2007/0074451 A1* | 4/2007 | Pearce | ..................... | C12N 1/04 47/57.6 |
| 2018/0228163 A1* | 8/2018 | Kang | ..................... | A01N 63/00 |
| 2018/0289001 A1* | 10/2018 | Lalgudi | ................. | A01N 25/00 |

FOREIGN PATENT DOCUMENTS

| | | | |
|---|---|---|---|
| CN | 1958532 A | 5/2007 | |
| CN | 101748088 A | 6/2010 | |
| CN | 101781629 A | 7/2010 | |
| CN | 102936574 A | * 2/2013 | ............ B09C 1/105 |
| CN | 102936574 A | 2/2013 | |
| CN | 104498410 A | 4/2015 | |
| CN | 105251763 A | 1/2016 | |
| CN | 105312310 A | 2/2016 | |
| CN | 108085272 A | 5/2018 | |
| JP | 2017163900 A | 9/2017 | |

OTHER PUBLICATIONS

Gano-Cohen et al., "Nonnodulating *Bradyrhizobium* spp. Modulate the Benefits of Legume-Rhizobium Mutualism", Applied and Environmental Microbiology, vol. 82, pp. 5259-5268 (Year: 2016).*
Kang et al. "The trapping of rhizobia in waste V—Ti magnetite mine soils and their symbiotic nitrogen-fixing effects", China Journal of Applied Environmental Biology, Apr. 25, 2016, pp. 0230-0235, vol. 22, No. 2, with partial English translation.
Zhao et al., "The Role of Leguminous Plants and Rhizobium in Ecological Environment", Agro-Environment & Development, Aug. 2013, pp. 7-12, vol. 30, No. 4. , with partial English translation.
Ahmad et al., "Metal and antibiotic resistance traits in *Bradyrhizobium* sp. (cajanus) isolated from soil receiving oil refinery wastewater", World Journal of Microbiology & Biotechnology, 2001, pp. 379-384, vol. 17, Kluwer Academic Publishers, The Netherlands.
Wani et al., "Effect of metal tolerant plant growth promoting *Bradyrhizobium* sp. (vigna) on growth, symbiosis, seed yield and metal uptake by greengram plants", Chemosphere, 2007, pp. 36-45, vol. 70, Elsevier Ltd.
Dary et al., "'In situ' phytostabilisation of heavy metal polluted soils using Lupinus luteus inoculated with metal resistant plant-grownth promoting rhizobacteria", Journal of Hazardous Materials, 2009, pp. 1-8, HAZMAT-11054, Elsevier.
Miao et al., "Tolerance to Lead-zinc Stress and16S rDNA PCR-RFLP of Rhizobia Isolated from Nodules of Leguminous Plants in Huize Lead zinc Mining Tailings", Acta Agriculturae Boreali occidentalis Sinica, 2011, pp. 89-93, vol. 20, No. 11, with partial English translation.
Zhou et al. "Effects of Three Kinds of Foreign Media Materials on the Activity of Alfalfa Rhizobium", Acta Agrestia Sinica, Nov. 2014, pp. 1288-1290, vol. 22, No. 6, with partial English translation.
Pang et al., "Application of Rare-earth Elements in the Agriculture of China and its Environmental Behavior in Soil", Journal of Soils & Sediments, Dec. 31, 2001, pp. 124-129, vol. 1, No. 2, Ecomed Publishers, Landsberg, Germany.
International Search Report issued for corresponding International Patent Application No. PCT/CN2018/117249, dated Feb. 27, 2019.
Written Opinion issued by the International Searching Authority for corresponding International Patent Application No. PCT/CN2018/117249, dated Apr. 3, 2019.
Xiaonian Huang "Effects of seed dressing with rhizobia and Rare Earth on Yield and Quality of Red Clover", http://www.cqvip.com, May 13, 2008, pp. 5-6 , vol. 32, No. 4, Guizhou Animal Science and Veterinary Medicine, with partial English translation.
Singh et al., "Optimization of Dairy Sludge for Growth of Rhizobium Cells", https://www.ncbi.nlm.nih.gov/pmc/articles/PMC37821216/, Sep. 9, 2013, pp. 1-13, doi 10.1155/2013/845264, Biomed Research International 2013.

\* cited by examiner

*Primary Examiner* — Michelle F. Paguio Frising
(74) *Attorney, Agent, or Firm* — Myers Wolin, LLC.

(57) ABSTRACT

Provided is a type of *Rhizobium* with the classified nomenclature of *BradyRhizobium* sp. KTMS 0001 or *BradyRhizobium* sp. KTMS 0002, and the deposit number of CCTCC No. M2017580 or CCTCC No. M2017581. Also provided are a bacterial preparation containing the *Rhizobium*, a method for restoring rare-earth tailings soil and a use of the *Rhizobium*.

4 Claims, 1 Drawing Sheet

Specification includes a Sequence Listing.

RHIZOBIUM AND USE AND BACTERIAL PREPARATION THEREOF, AND METHOD FOR RESTORING RARE-EARTH TAILING SOIL OR SILICA ORE TAILING WASTE

CROSS REFERENCE TO RELATED APPLICATIONS

The present application is a U.S. National Phase of International Patent Application Serial No. PCT/CN2018/117249 filed on Nov. 23, 2018, which claims priority to Chinese Application No. 201711261668.1, filed on Dec. 4, 2017, the contents of each of which are incorporated by reference in their entirety for all purposes.

The material in the ASCII text file inno_10053_20200529_sequence_listing, filed with the present application via EFS-web, created on May 15, 2020, having the size of 1000 bytes, is incorporated by reference in the specification for all purposes.

FIELD OF THE INVENTION

The present invention relates to the field of biological engineering, in particular to a *Rhizobium*, a bacterial preparation comprising the same, a method for restoring rare-earth tailings soil or silicon ore tailings waste and use of the *Rhizobium*.

BACKGROUND OF THE INVENTION

Rare-earth elements refer to lanthanide elements with atomic numbers of 57 to 71 in the periodic table of chemical elements as well as scandium (Sc) element and yttrium (Y) element with similar properties. The rare-earth elements are a group of 17 elements, called industrial vitamins, and can be widely used in industrial, agricultural and electronic fields. The rare-earth elements mainly exist in rare-earth ore in the form of rare-earth oxides or rare-earth ions, and can be extracted by tank leaching, heap leaching and in-situ leaching. It is difficult to restore the damaged vegetation after ore extraction, and it is difficult to treat the heaped slag after leaching. The related data shows that for each ton of mixed rare-earths obtained by extracting rare-earth via tank leaching, 200 square meters of surface vegetation will be destroyed, 300 cubic meters of surface soil will be stripped, and 2000 cubic meters of tailings will be formed, resulting in 12 million cubic meters of water and soil erosion per year.

The damage of rare-earth extraction to vegetation, soil and groundwater will seriously affect the local ecological environment. During the extraction process, heavy metals, fluorine, ammonia nitrogen and sulfate ions as well as lots of tailings and waste rock deposit, seriously destroy the original ecology of the mine and result in water and soil erosion. The release and migration of these pollution sources will cause serious pollution to the nearby soil, and even the downstream rivers and lakes, groundwater fields and other ecological environments, cause ecological environment deterioration and threaten human health.

As an extremely severely degraded soil, the ecological restoration of (waste) rare-earth ore attracts high attention at home and abroad. This kind of soil character destruction usually comprises that severe desertification and extreme infertility, water and fertilizer retention capacity are poor, organic matters and other soil essential elements are lack, and soil microbial diversity is seriously damaged. Thus, it is extremely difficult for plants to grow on such harsh soils. There are few successful cases of vegetation restoration of rare-earth mines. Plants-microorganisms interaction joint restoration as the main body of the ecological restoration can be widely used in ecological restoration engineering of polluted tailings. The prior art mostly pads thick borrowed soil and planting eucalyptus and pine trees on the borrowed soil. However, the prior art cannot improve the soil quality, and the survival rate of plants is often not high. Symbiotic nitrogen fixation by the *Rhizobium* and leguminous plants is the most powerful plant microorganism interaction system in nature. In addition, the *Rhizobium* can also play a role in promoting bacteria, which can promote plant growth and improve soil quality. Legumes and *Rhizobium* nitrogen fixation as pioneer plants can thrive on harsh soils lack of moisture and nutrients. Utilizing the nitrogen fixation effect of the *Rhizobium*-legume interaction symbiotic system to accelerate the accumulation of nitrogen in the waste rare-earth ore soil, thereby promoting the circulation and accumulation of nutrients, is the preferred strategy for the ecological restoration of the waste rare-earth ore.

The *Rhizobium* is a kind of aerobic gram-negative bacteria, which is symbiotic with legumes, forms nodules and fixes nitrogen in the air for plant nutrition. The normal cells of the *Rhizobium* move with flagella, are free of spore, can utilize a variety of carbohydrates, and generate a considerable amount of extracellular mucus. Both *Rhizobium* and *Bradyrhizobium* can invade the roots of leguminous plants to form root nodules, and become branched polymorphic cells in the nodules, i.e., to form mycelia.

CN102936574A discloses a *Rhizobium* W33, which has the classified nomenclature of *Rhizobium* sp. W33, deposited at the China Center for Type Culture Collection on Sep. 18, 2012 with the deposit number of CCTCC No. M2012357. This *Rhizobium* can promote the growth of *Eragrostis curvula* on waste rare-earth tailings soil. Specifically, the *Rhizobium* W33 can promote significant increase in root length and plant height of *Eragrostis curvula* by 19% and 46% higher than the control, respectively. There was no significant increase in plant dry weight. The inoculation of the *Rhizobium* W33 (CCTCC NO: M2012357) makes the plant roots developed, and the amount of sand fixation increased by 98%, which is beneficial to the soil and water conservation of the waste rare-earth tailings. In addition, the *Rhizobium* W33 can significantly promote the growth of *Medicago sativa* in heavy metal polluted soil. Compared with the control of sterilized bacterial preparation, the inoculation of the bio-restoration bacterial preparation with the *Rhizobium* W33 as an active ingredient significantly increases the plant height of *Medicago sativa* by 1.7 times, and the root weight and dry weight of the aerial part by 2.7 and 2.4 times, respectively.

However, in the practical application, it has been found that the *Rhizobium* W33 (CCTCC NO. M2012357) on plant growth promotion is still very limited and unsatisfactory, and there is no obvious growth promotion effect after 6 months. Therefore, it is difficult to achieve efficient long-term practical application effect on restoration of rare-earth tailings soil.

SUMMARY OF THE INVENTION

An object of the present invention is to provide a *Rhizobium* which can efficiently and long-termly promote legume growth in rare-earth tailings soil, thereby efficiently and long-termly restoring the rare-earth tailings soil.

In order to achieve the above object, in one aspect, the present invention provides the *Rhizobium*. The *Rhizobium* has the classified nomenclature of *Bradyrhizobium* sp.

KTMS 0001 or *Bradyrhizobium* sp. KTMS 0002, and the *Rhizobium* is deposited in CCTCC with the deposit number of CCTCC No. M2017580 or CCTCC No. M2017581.

In a further aspect, the present invention also provides a *Rhizobium* bacterial preparation comprising a culture medium and the *Rhizobium* as described above.

In a further aspect, the present invention also provides a method for restoring rare-earth tailings soil or silicon ore tailings waste. The method includes seeding legumes on the rare-earth tailings soil or silicon ore tailings waste and inoculating the *Rhizobium* as mentioned above.

In a further aspect, the present invention also provides use of the *Rhizobium* as described above in the restoration of rare-earth tailings soil or silicon ore tailings waste.

Through the above-mentioned technical scheme, the *Rhizobium* of the invention can greatly and long-termly increase the fresh and dry weight of plants grown in the rare-earth tailings soil. For example, the dry weight of the underground part of *Stylosanthes guianensi* planted in the rare-earth tailings soil for 9 months can be increased by 16.7 times, and the dry weight of the aerial part thereof can be increased by 12.8 times, so as to efficiently and long-termly restore the rare-earth tailings soil.

Other features and advantages of the present invention will be described in detail in the following detailed description.

Biomaterial Deposition Information

The *Rhizobium* classified as *Bradyrhizobium* sp. KTMS 0001 is deposited at the China center for type culture collection at Wuhan University, Wuhan, China, on Oct. 13, 2017, and deposited with the deposit number of CCTCC No. M2017580.

The *Rhizobium* classified as *Bradyrhizobium* sp. KTMS 0002 is deposited at the China center for type culture collection at Wuhan University, Wuhan, China, on Oct. 13, 2017, and deposited with the deposit number of CCTCC No. M2017581.

BRIEF DESCRIPTION OF THE DRAWINGS

The drawings are provided for further understanding of the present invention and constitute a part of the specification, together with the following detailed description serve to explain the embodiments of the present invention, but not limit the present invention. In the drawings:

FIG. 1 is a comparison chart of the growth of *Cassia tora* (4-6th from left) treated with the *Rhizobium* with deposit number of CCTCC No. M2017581 and *Cassia tora* (1-3th from left) treated with a sterilized 10 mM magnesium sulfate aqueous solution, after being planted in the rare-earth tailings soil for 9 months.

DETAILED DESCRIPTION OF THE EMBODIMENTS

Hereinafter, specific embodiments of the present invention will be described in detail with reference to the drawings. It should be understood that the specific embodiments described herein are only intended to illustrate the present invention and are not intended to limit the present invention.

In one aspect, the present invention provides a *Rhizobium*. The *Rhizobium* has the classified nomenclature of *Bradyrhizobium* sp. KTMS 0001 or *Bradyrhizobium* sp. KTMS 0002, and the *Rhizobium* is deposited in CCTCC with the deposit number of CCTCC No. M2017580 or CCTCC No. M2017581.

The *Rhizobium* with the deposit number of CCTCC No. M2017580 is one of 15 strains of rhizobia separated from a rare-earth tailings sample from Guangdong by a plant capture method. The *Rhizobium* with the deposit number of CCTCC No. M2017581 is one of 15 strains of rhizobia separated from a rare-earth tailings sample from Jiangxi by the plant capture method.

In a further aspect, the present invention provides the *Rhizobium* bacterial preparation comprising a culture medium and the above-mentioned *Rhizobium*.

Wherein, the dosage form of the *Rhizobium* bacterial preparation may be a seed soaking solution, dry powder or mud-like substance.

Optionally, in the *Rhizobium* bacterial preparation, the number of the *Rhizobium* is $(2\text{-}20) \times 10^9$ CFU per gram of the bacterial preparation.

Optionally, the culture medium comprises a YMB (yeast mannitol broth) culture medium and/or a MAG (magnesium) culture medium.

Optionally, the *Rhizobium* bacterial preparation further comprises an auxiliary agent, and the auxiliary agent comprises a surfactant and/or a solid carrier; the surfactant comprises at least one of sodium dodecyl benzene sulfonate, sodium ligninsulfonate and polycondensate of sodium alkylnaphthalene sulfonate; and the solid carrier comprises at least one of peat, vermiculite, bran flour, wheat bran, kaolin, diatomite, white carbon black, talc and fine sand.

Preferably, the *Rhizobium* with the deposit number of CCTCC No. M2017580 or CCTCC No. M2017581 can be cultured in a YMB medium to obtain a culture solution with a bacterial concentration of $100 \times 10^9$ CFU/mL, and then the culture solution and the auxiliary agent (sodium dodecyl benzene sulfonate and kaolin) are mixed to prepare the bacterial preparation. The amount of sodium dodecyl benzene sulfonate is 50-200 g per liter of the culture solution, and the amount of kaolin is 200-400 g per liter of the culture solution.

In a further aspect, the present invention also provides a method for restoring rare-earth tailings soil or silicon ore tailings waste. The method includes seeding legume on the rare-earth tailings soil or silicon ore tailings waste, and inoculating the above-mentioned *Rhizobium*.

Optionally, the inoculation amount of the *Rhizobium* is $(1\text{-}10) \times 10^9$ CFU per square meter of bare surface of the rare-earth tailings soil or the silicon ore tailings waste.

Optionally, the legume includes at least one of *Arachis hypogaea, Cassia tora, Stylosanthes guianensi* and *Medicago Sativa*.

In a further aspect, the present invention also provides an application of the *Rhizobium* in restoration of rare-earth tailings soil or silicon ore tailings waste.

Optionally, in the above-mentioned application, the legume is sown on the rare-earth tailings soil or silicone ore tailings waste, and the *Rhizobium* is inoculated.

Hereinafter, the present invention is described in detail based on embodiments. In the following embodiments, a polluted rare-earth tailings soil is a sample from Qingyuan, Guangdong.

Embodiment 1

In embodiment 1, a soil restoration experiment is performed on the rare-earth tailings soil by using the *Rhizobium* with the deposit number of CCTCC No. M2017580.

The test plants are legume, in particular, *Stylosanthes guianensi Arachis hypogaea, Medicago Sativa*, and *Cassia* tora. Each kind of the plant is divided into 10 inoculating groups and 3 control groups. The seeds are sterilized by sterilizing with ethanol for 30 mM and washing with aseptic water for 5 times. The seeds of the inoculating groups are soaked in a $100 \times 10^9$ CFU/ml solution of the *Rhizobium* with the deposit number of CCTCC No. M2017580 (*Rhizobium* 1) and 9 strains of *Rhizobium* (*Rhizobium* 2-10) separated with the above *Rhizobium* together. Control Group 1 adopts a sterilized 10 mM magnesium sulfate aqueous solution instead of the *Rhizobium* solution, and the rest condition is the same. Control Group 2 adopts a $100 \times 10^9$ CFU/ml solution of a commercial *Rhizobium* bacterial preparation produced by Panzhihua Xiyu biotech Co., Ltd. instead of the *Rhizobium* solution. Control Group 3 adopts a $100 \times 10^9$ CFU/ml solution of a commercial EM bacterial preparation produced by Ningdu Junmima biotech Co., Ltd. instead of the *Rhizobium* solution. The seeds are sown into flowerpots filled with the polluted rare-earth tailings soil, then the flowerpots are moved to a greenhouse for cultivation, and the same amount of water is irrigated to keep the soil moist. The dry weights of the aerial part and the underground part in each flowerpot are measured after 9 months, respectively, and the result is shown in Table 1. According to the Table 1, compared with the treatment with aseptic water, the dry weights of the aerial part and the underground part of *Cassia tora* grown in the rare-earth tailings soil treated by using the *Rhizobium* with the deposit number of CCTCC No. M2017580 (*Rhizobium* 1) for 9 months are increased by 13.2 times and 11.6 times, respectively. FIG. 1 representatively shows the growth comparison of the *Cassia tora* (4-6th from left) treated with the *Rhizobium* with the deposit number of CCTCC No. M2017580 (*Rhizobium* 1) and the *Cassia tora* (1-3th from the left) treated with sterilized magnesium sulfate aqueous solution after being planted in the rare-earth tailings soil for 9 months. And, compared with the 9 strains of *Rhizobium* (*Rhizobium* 2-10) separated with the *Rhizobium* together, the commercial *Rhizobium* bacterial preparation produced by Panzhihua Xiyu biotech Co., Ltd. and the commercial EM bacterial preparation produced by Ningdu Junmima biotech Co., Ltd., the *Rhizobium* with the deposit number of CCTCC No: M2017580 (*Rhizobium* 1) has a significantly enhanced capacity to promote the plant growth.

TABLE 1

| | Dry weight (g) | | | | | | | |
|---|---|---|---|---|---|---|---|---|
| | *Stylosanthes guianensi* | | *Arachis hypogaea* | | *Cassia tora* | | *Medicago Sativa* | |
| Soaking solution | Aerial part | Underground part | Aerial part | Underground part | Aerial part | Underground part | Aerial part | Underground part |
| Sterilized 10 mM magnesium sulfate aqueous solution | 1.2 | 0.8 | 1.1 | 0.5 | 0.9 | 1.1 | 0.8 | 0.5 |
| Rhizobium 1 | 15.3 | 13.4 | 6.0 | 4.2 | 11.9 | 12.8 | 3.1 | 2.2 |
| Rhizobium 2 | 8.3 | 8.4 | 3.3 | 3.0 | 8.3 | 8.4 | 2.0 | 0.9 |
| Rhizobium 3 | 7.2 | 7.0 | 4.0 | 3.2 | 3.8 | 6.0 | 1.8 | 0.8 |
| Rhizobium 4 | 9.4 | 6.8 | 3.8 | 3.2 | 7.5 | 8.0 | 2.1 | 1.2 |
| Rhizobium 5 | 5.2 | 1.4 | 2.6 | 2.2 | 6.5 | 7.2 | 1.9 | 1.1 |
| Rhizobium 6 | 7.5 | 3.2 | 3.6 | 3.1 | 4.6 | 7.3 | 1.8 | 1.0 |
| Rhizobium 7 | 8.3 | 5.7 | 3.2 | 3.9 | 5.6 | 6.8 | 2.0 | 1.0 |
| Rhizobium 8 | 9.5 | 8.5 | 3.5 | 3.0 | 8.8 | 9.8 | 2.2 | 1.0 |
| Rhizobium 9 | 9.8 | 4.6 | 3.8 | 3.0 | 6.7 | 7.8 | 2.1 | 1.2 |
| Rhizobium 10 | 8.6 | 5.0 | 4.1 | 3.3 | 5.9 | 7.0 | 1.6 | 0.8 |
| Control Group 2 | 8.8 | 5.2 | 2.3 | 1.8 | 4.5 | 3.8 | 1.5 | 0.7 |
| Control Group 3 | 1.5 | 0.7 | 2.0 | 1.2 | 2.2 | 1.0 | 0.9 | 0.5 |

Embodiment 2

In embodiment 2, a soil restoration experiment is performed on the rare-earth tailings soil by using the *Rhizobium* with the deposit number of CCTCC No. M2017581.

The test plants are legume, in particular, *Stylosanthes guianensi Arachis hypogaea, Medicago Sativa*, and *Cassia tora*. Each kind of the plant is divided into 10 inoculating groups and one control group. The seeds are sterilized by sterilizing with ethanol for 30 min and washing with aseptic water for 5 times. The seeds of the inoculating groups are soaked in a $100 \times 10^9$ CFU/ml solution of the *Rhizobium* with the deposit number of CCTCC No. M2017581 (*Rhizobium* 11) and 9 strains of *Rhizobium* (*Rhizobium* 12-20) separated with the above *Rhizobium* together. Control Group 1 adopts a sterilized 10 mM magnesium sulfate aqueous solution instead of the *Rhizobium* solution. Control Group 2 adopts a $100 \times 10^9$ CFU/ml solution of a commercial *Rhizobium* bacterial preparation produced by Panzhihua Xiyu biotech Co., Ltd. instead of the *Rhizobium* solution. Control Group 3 adopts a $100 \times 10^9$ CFU/ml solution of a commercial EM bacterial preparation produced by Ningdu Junmima biotech Co., Ltd. instead of the *Rhizobium* solution. The seeds are sown into flowerpots filled with the polluted rare-earth tailings soil, then the flowerpots are moved to a greenhouse for cultivation, and the same amount of water is irrigated to keep the soil moist. The dry weights of the aerial part and the underground part in each flowerpot are measured after 9 months, respectively, and the result is shown in Table 2. According to the Table 2, compared with the treatment with aseptic water, the dry weights of the aerial part and the underground part of *Cassia tora* grown in the rare-earth tailings soil treated by using the *Rhizobium* with the deposit number of CCTCC No. M2017581 (*Rhizobium* 11) for 9 months are increased by 12.9 times and 14.8 times, respectively. And, compared with the 9 strains of *Rhizobium* (*Rhizobium* 12-20) separated with the 11th *Rhizobium* together, the commercial *Rhizobium* bacterial preparation produced by Panzhihua Xiyu biotech Co., Ltd. and the commercial EM bacterial preparation produced by Ningdu Junmima biotech Co., Ltd., the deposit number of CCTCC No: M2017581 (*Rhizobium* 11) has a significantly enhanced capacity to promote the plant growth.

TABLE 2

| Soaking solution | Dry weight (g) | | | | | | | |
|---|---|---|---|---|---|---|---|---|
| | *Stylosanthes guianensi* | | *Arachis hypogaea* | | *Cassia tora* | | *Medicago Sativa* | |
| | Aerial part | Underground part | Aerial part | Underground part | Aerial part | Underground part | Aerial part | Underground part |
| Sterilized 10 mM magnesium sulfate aqueous solution | 1.2 | 0.9 | 1.0 | 0.5 | 1.4 | 1.3 | 0.8 | 0.6 |
| Rhizobium 11 | 15.5 | 13.3 | 6.1 | 4.1 | 11.4 | 12.5 | 3.0 | 2.2 |
| Rhizobium 12 | 8.4 | 8.3 | 3.4 | 2.9 | 8.2 | 8.5 | 2.0 | 0.9 |
| Rhizobium 13 | 7.3 | 6.9 | 4.1 | 3.1 | 3.8 | 6.1 | 1.8 | 0.8 |
| Rhizobium 14 | 9.5 | 6.7 | 3.9 | 3.1 | 7.4 | 8.1 | 2.1 | 1.2 |
| Rhizobium 15 | 5.3 | 1.4 | 2.7 | 2.2 | 6.4 | 7.3 | 1.9 | 1.1 |
| Rhizobium 16 | 7.6 | 3.2 | 3.7 | 3.0 | 4.6 | 7.4 | 1.8 | 1.0 |
| Rhizobium 17 | 8.4 | 5.6 | 3.3 | 3.8 | 5.5 | 6.9 | 2.0 | 1.0 |
| Rhizobium 18 | 9.6 | 8.4 | 3.6 | 2.9 | 8.7 | 9.9 | 2.2 | 1.0 |
| Rhizobium 19 | 9.9 | 4.6 | 3.9 | 2.9 | 6.6 | 7.9 | 2.1 | 1.2 |
| Rhizobium 20 | 8.7 | 5.0 | 4.2 | 3.2 | 5.8 | 7.1 | 1.8 | 0.8 |
| Control Group 2 | 7.8 | 5.8 | 2.0 | 1.7 | 5.0 | 4.0 | 1.9 | 0.9 |
| Control Group 3 | 1.2 | 1.0 | 1.8 | 0.9 | 3.1 | 1.8 | 0.7 | 0.5 |

Embodiment 3

The embodiment is used for illustrating the application of the *Rhizobium* with the deposit number of CCTCC No. M2017580 (*Rhizobium* 1) and the 11th *Rhizobium* with the deposit number of CCTCC No. M2017581 (*Rhizobium* 11) in the rare-earth tailings for soil restoration and re-greening.

Firstly, the *Rhizobium* with the deposit number of CCTCC No. M2017580 and the *Rhizobium* with the deposit number of CCTCC No. M2017581 are cultured in YMB culture medium to obtain a culture solution with bacterial concentration of $100 \times 10^9$ CFU/ml, respectively, and then the culture solution is mixed with the auxiliary agent (sodium dodecyl benzene sulfonate and kaolin) to prepare the bacterial preparation. For each liter of the culture solution, the amount of sodium dodecyl benzene sulfonate is 100 g, and the amount of kaolin is 300 g.

Rare-earth tailings are used for soil restoration and re-greening by finishing, punching, planting, inoculation and fertilization in sequence, wherein the punching step includes digging 10 cm×10 cm pits at a distance of 40 cm; the planting step includes sowing 3-20 *Stylosanthes* seeds; the inoculation step includes applying 1 g bacterial preparation to each pit; and the fertilization step includes filling the pits to the soil surface with soil. For each pit, 0.5 kg organic fertilizer is applied completely and uniformly without piling up. Experimental Group 1 is a bacterial preparation prepared from the culture solution of the *Rhizobium* with the deposit number of CCTCC No. M2017580, and Experimental Group 2 is a bacterial preparation prepared from the culture solution of the *Rhizobium* with the deposit number of CCTCC No. M2017581. Control Group 1 only adopts aseptic water instead of the culture solution. Control Group 2 adopts a commercial *Rhizobium* bacterial preparation produced by Xiyu biotech Co., Ltd. instead of the bacterial preparation. Control Group 3 adopts a commercial EM bacterial preparation produced by Junmima biotech Co., Ltd. instead of the bacterial preparation.

After 9 months of restoration and regreening, the fresh weight of all vegetations on the rare-earth tailings soil per unit area of restoration are measured. The result shows that the fresh weight of all vegetations per square meter of rare-earth tailings soil in Experimental Group 1 is 112.1 kg, and the fresh weight thereof in Experimental Group 2 is 109.3 kg, but the fresh weight thereof in Control Groups 1-3 are only 65.3 kg, 80.2 kg and 70.5 kg, respectively. Thus, the *Rhizobium* with the deposit number of CCTCC No. M2017580 and the *Rhizobium* with the deposit number of CCTCC No. M2017581 can efficiently and long-termly restore the rare-earth tailings soil.

The rhizosphere soils of *Stylosanthes* planted in Experimental Groups 1, 2 and Control Groups 1-3 are selected, and 16S rDNA library construction and microbial diversity analysis are performed on the soil microorganisms, and the scheme is as follows:

Construction of 16S rDNA Cloning Library

The total DNA of extracted soil microorganisms is amplified by using 16S rDNA primer, which includes primer 27F with a sequence of AGAGTTTGATCCTGGCTCAG shown as SEQ ID NO.1 and primer 1483R with a sequence of GGTTACCTTGTTACGACTT shown as SEQ ID NO.2, 16S bands are recovered, and the target fragment is connected with the vector by using a pMD19-T vector kit to obtain recombinant plasmid DNA. The recombinant plasmid DNA solution is added into suspension of competent cells (JM109 *E. coli*), transformation is performed, Amp resistance screening is carried out, screened single colonies are selected to be subjected to culturing in an LB liquid culture medium under shaking overnight. Plasmids are extracted by using a plasmid extraction kit. Then positive plasmids from cloning are sequenced to obtain the sequence of 16S rDNA.

The obtained 16S rDNA sequence is compared online by NCBI Blast to find the most similar sequence of each sequence in GenBank. Then the reference sequence is selected, and is compared by ClustalX program together with the 16SrDNA sequence. The phylogenetic tree is constructed by using MEGA 5.0 software via the Neighbor-Joining method, and the phylogenetic tree is inspected with repeat number of 1000. The soil microbial diversity index is calculated according to the Shannon-wiener diversity index method. The soil microbial diversity indexes of the rhizosphere soil of *Stylosanthes* planted in Experimental Groups 1, 2 and Control Groups 1-3 are shown in Table 3. According to the data in Table 3, the microbial diversity of Experimental Groups 1 and 2 is significantly higher than that of Control Groups 1-3. Thus, the *Rhizobium* with the deposit number of CCTCC No. 2017580 and the *Rhizobium* with the deposit number of CCTCC No. 2017581 can efficiently and long-termly restore the microbial diversity of the rare-earth tailings soil.

TABLE 3

| Restored soil | Soil microbial diversity index |
|---|---|
| Experimental Group 1 | 6.12 |
| Experimental Group 2 | 6.08 |
| Control Group 1 | 2.27 |

TABLE 3-continued

| Restored soil | Soil microbial diversity index |
|---|---|
| Control Group 2 | 4.21 |
| Control Group 3 | 3.82 |

After restoration and re-greening for 9 months, the nitrogen/phosphorus and heavy metals contents of rhizosphere soil of *Stylosanthes* are detected, and the heavy metal content of the aerial part of *Stylosanthes* is detected. The results are shown in Tables 4 and 5.

TABLE 4

| | Element content in rhizosphere soil (mg/kg) | | | | | | | |
|---|---|---|---|---|---|---|---|---|
| Restored soil | Total nitrogen | Total phosphorus | Cd | Hg | As | Pb | Cr | Cu |
| Experimental Group 1 | 205 | 343 | 0.112 | 0.0056 | 3.54 | 23.54 | 43.33 | 52.48 |
| Experimental Group 2 | 266 | 351 | 0.117 | 0.0056 | 4.07 | 25.81 | 44.21 | 52.64 |
| Control Group 1 | 78 | 279 | 0.193 | 0.0152 | 5.52 | 40.85 | 46.72 | 53.66 |
| Control Group 2 | 114 | 311 | 0.122 | 0.0058 | 5.21 | 24.42 | 44.18 | 58.14 |
| Control Group 3 | 103 | 306 | 0.125 | 0.0097 | 5.13 | 26.07 | 49.07 | 54.47 |

TABLE 5

| | Element content of aerial part of Stylosanthes (mg/kg) | | | | | | | |
|---|---|---|---|---|---|---|---|---|
| Restored soil | Total nitrogen | Total phosphorus | Cd | Hg | As | Pb | Cr | Cu |
| Experimental Group 1 | 19878 | 1207 | 0.140 | 0.0015 | 0.166 | 2.250 | 4.85 | 4.16 |
| Experimental Group 2 | 16271 | 990 | 0.130 | 0.0014 | 0.063 | 2.807 | 4.50 | 3.73 |
| Control Group 1 | 10803 | 578 | 0.220 | 0.0015 | 0.444 | 2.962 | 5.60 | 6.07 |
| Control Group 2 | 15735 | 820 | 0.262 | 0.0023 | 0.187 | 5.082 | 4.85 | 5.76 |
| Control Group 3 | 13748 | 830 | 0.261 | 0.0014 | 0.514 | 2.918 | 8.40 | 8.22 |

According to the data in Tables 4 and 5, the *Rhizobium* with the deposit number of CCTCC No. 2017580 and the *Rhizobium* with the deposit number of CCTCC No. 2017581 can effectively enrich nitrogen and phosphorus in the rhizosphere soil, but not enrich heavy metals, and also not enrich heavy metals of the aerial part of *Stylosanthes*, so that they can be used as feed. Thus, the *Rhizobium* with the deposit number of CCTCC No. 2017580 and the *Rhizobium* with the deposit number of CCTCC No. 2017581 can also bring considerable economic benefits to soil restoration.

The preferred embodiments of the present invention have been described in detail with reference to the accompanying drawings. However, the present invention is not limited to the specific details in the above embodiments. Within the scope of the technical concept of the present invention, the technical schemes of the present invention can be subjected to simple modifications, and these simple modifications all belong to the protection scope of the present invention.

Further to be noted that, in various specific features of the above-described specific embodiments described, may be combined in any suitable manner without conflict. To avoid unnecessary repetition, the present invention will not further descript the various possible combinations.

Further, among various embodiments of the present invention may be arbitrarily combined as long as it does not violate the spirit of the invention, which should also be considered as the disclosure of the present invention.

What is claimed is:

1. A *Rhizobium*, wherein the *Rhizobium* has a classified nomenclature of *Bradyrhizobium* sp. KTMS 0001 or *Bradyrhizobium* sp. KTMS 0002, and has deposit number of China Center for Type Culture Collection (CCTCC) No. M2017580 or CCTCC No. M2017581, wherein said *Rhizobium* is cultured in a YMB medium to obtain a culture solution with a *Rhizobium* concentration of $100 \times 10^9$ Colony Forming Units (CFU) per mL, used in restoration of rare earth tailings soil or silicon ore tailings waste.

2. A *Rhizobium* bacterial preparation, wherein the *Rhizobium* bacterial preparation comprises a culture medium consisting of the YMB culture medium and/or a MAG culture medium, and the *Rhizobium* according to claim 1, wherein the *Rhizobium* bacterial preparation further comprises an auxiliary agent, which comprises a surfactant and a solid carrier; wherein the surfactant comprises at least one of sodium ligninsulfonate and polycondensate of sodium alkylnaphthalene sulfonate; and the solid carrier comprises at least one of peat, vermiculite, rice bran flour, wheat bran, kaolin, diatomite, white carbon black, talc and fine sand, wherein in the *Rhizobium* bacterial preparation the amount of the *Rhizobium* is $(2\text{-}20) \times 10^9$ CFU per gram of the bacterial preparation, and wherein a dosage form of the *Rhizobium* bacterial preparation is a seed soaking solution, dry powder or mud-like substance.

3. A method for restoring rare earth tailings soil or silicon ore tailings waste, comprising:

seeding legumes on the rare earth tailings soil or silicon ore tailings waste; and inoculating the seeded soil or waste with the *Rhizobium* according to claim 1.

4. The method according to claim 3, wherein the legume comprises at least one of *Arachis hypogaea, Cassia* tora, *Stylosanthes guianensi* and *Medicago Sativa.*

* * * * *

SEQUENCE LISTING

<160> NUMBER OF SEQ ID NOS: 2

<210> SEQ ID NO 1
<211> LENGTH: 20

```
<212> TYPE: DNA
<213> ORGANISM: Artificial Sequence
<220> FEATURE:
<223> OTHER INFORMATION: This sequence is synthesized in lab.

<400> SEQUENCE: 1
agagtttgat cctggctcag                                               20

<210> SEQ ID NO 2
<211> LENGTH: 19
<212> TYPE: DNA
<213> ORGANISM: Artificial Sequence
<220> FEATURE:
<223> OTHER INFORMATION: This sequence is synthesized in lab.

<400> SEQUENCE: 2
ggttaccttg ttacgactt                                                19
```